(12) United States Patent
Chamorro, III et al.

(10) Patent No.: US 9,636,245 B2
(45) Date of Patent: May 2, 2017

(54) TRANSPYLORIC ANCHORING

(71) Applicant: GI DYNAMICS, INC., Lexington, MA (US)

(72) Inventors: Andres Chamorro, III, Ashland, MA (US); Andy H. Levine, Newton, MA (US); David A. Melanson, Hudson, NH (US); Barry Maxwell, Spencer, MA (US); Richard A. Gambale, Tyngsboro, MA (US)

(73) Assignee: GI Dynamics, Inc., Boston, MA (US)

( * ) Notice: Subject to any disclaimer, the term of this patent is extended or adjusted under 35 U.S.C. 154(b) by 0 days.

(21) Appl. No.: 14/414,606

(22) PCT Filed: Jul. 12, 2013

(86) PCT No.: PCT/US2013/050346
§ 371 (c)(1),
(2) Date: Jan. 13, 2015

(87) PCT Pub. No.: WO2014/012041
PCT Pub. Date: Jan. 16, 2014

(65) Prior Publication Data
US 2015/0190259 A1    Jul. 9, 2015

Related U.S. Application Data

(60) Provisional application No. 61/671,470, filed on Jul. 13, 2012.

(51) Int. Cl.
*A61M 5/00*       (2006.01)
*A61F 5/00*        (2006.01)
*A61F 2/04*        (2013.01)

(52) U.S. Cl.
CPC .............. *A61F 5/0036* (2013.01); *A61F 2/04* (2013.01); *A61F 5/0076* (2013.01);
(Continued)

(58) Field of Classification Search
CPC .... A61F 5/0076; A61F 5/0079; A61F 5/0089; A61F 2/04; A61F 2/24; A61F 5/0083;
(Continued)

(56) References Cited

U.S. PATENT DOCUMENTS 4,134,405 A    1/1979    Smit
4,878,905 A    11/1989   Blass
(Continued)

FOREIGN PATENT DOCUMENTS

WO    WO 2004/049982 A2    6/2004
WO    WO 2009/130619 A1    10/2009
(Continued)

OTHER PUBLICATIONS

International Search Report issued in International Application No. PCT/2013/050346, entitled "Transpyloric Anchoring," Date of Search: Oct. 10, 2013.
(Continued)

*Primary Examiner* — Philip R Wiest
(74) *Attorney, Agent, or Firm* — Clark & Elbing LLP

(57) ABSTRACT

A gastrointestinal implant device (2800) comprises a planar proximal element (220) configured to reside in a stomach to resist distal migration, a distal element (222) configured to reside in an intestine to resist proximal migration and one or more tethers (224) coupling the planar proximal element to the distal element.

45 Claims, 7 Drawing Sheets

(52) U.S. Cl.
CPC .......... *A61F 5/0079* (2013.01); *A61F 5/0089* (2013.01); *A61F 2002/045* (2013.01)

(58) Field of Classification Search
CPC ........ A61F 2002/044; A61F 2220/0008; A61F 5/0036; A61M 27/002; A61B 17/1114
USPC ............................. 604/8–10; 623/23.64–23.7
See application file for complete search history.

(56) References Cited

U.S. PATENT DOCUMENTS

| | | | |
|---|---|---|---|
| 5,820,584 | A | 10/1998 | Crabb |
| 7,160,312 | B2 | 1/2007 | Saadat |
| 7,347,875 | B2 | 3/2008 | Levine et al. |
| 7,766,973 | B2 | 8/2010 | Levine et al. |
| 7,771,382 | B2 | 8/2010 | Levine et al. |
| 7,931,693 | B2 | 4/2011 | Binmoeller |
| 8,038,720 | B2 | 10/2011 | Wallace et al. |
| 8,057,420 | B2 | 11/2011 | Meade et al. |
| 8,114,045 | B2 | 2/2012 | Surti |
| 2003/0040804 | A1 | 2/2003 | Stack et al. |
| 2004/0019388 | A1 | 1/2004 | Starkebaum |
| 2004/0093065 | A1 | 5/2004 | Yachia |
| 2004/0220682 | A1 | 11/2004 | Levine et al. |
| 2005/0055039 | A1 | 3/2005 | Burnett et al. |
| 2005/0125020 | A1 | 6/2005 | Meade et al. |
| 2006/0142731 | A1 | 6/2006 | Brooks |
| 2006/0190019 | A1 | 8/2006 | Gannoe |
| 2007/0135825 | A1 | 6/2007 | Binmoeller |
| 2007/0173869 | A1 | 7/2007 | Gannoe et al. |
| 2007/0208360 | A1 | 9/2007 | Demarais et al. |
| 2008/0208239 | A1 | 8/2008 | Annunziata |
| 2008/0255678 | A1 | 10/2008 | Cully et al. |
| 2009/0093839 | A1 | 4/2009 | Kelleher |
| 2009/0182355 | A1 | 7/2009 | Levine et al. |
| 2009/0259236 | A2 | 10/2009 | Burnett et al. |
| 2010/0049224 | A1 | 2/2010 | Vargas |
| 2010/0204723 | A1 | 8/2010 | Gertner |
| 2010/0241146 | A1 | 9/2010 | Stack et al. |
| 2010/0286628 | A1 | 11/2010 | Gross |
| 2010/0298632 | A1 | 11/2010 | Levine et al. |
| 2010/0305590 | A1 | 12/2010 | Holmes et al. |
| 2011/0004228 | A1* | 1/2011 | Priplata .............. A61B 17/3468 606/153 |
| 2011/0004230 | A1 | 1/2011 | Levine et al. |
| 2011/0004320 | A1 | 1/2011 | Priplata et al. |
| 2011/0046537 | A1 | 2/2011 | Errico et al. |
| 2011/0066175 | A1 | 3/2011 | Gross |
| 2011/0098730 | A1 | 4/2011 | Kelleher |
| 2011/0106273 | A1 | 5/2011 | Belhe et al. |
| 2011/0118650 | A1 | 5/2011 | Nihalani |
| 2011/0190905 | A1 | 8/2011 | Behan |
| 2011/0213469 | A1 | 9/2011 | Chin et al. |
| 2011/0218563 | A1 | 9/2011 | Brooks et al. |
| 2011/0257580 | A1 | 10/2011 | Meade et al. |
| 2011/0276091 | A1 | 11/2011 | Melanson et al. |
| 2012/0004676 | A1 | 1/2012 | Vargas |
| 2012/0095384 | A1 | 4/2012 | Babkes |

FOREIGN PATENT DOCUMENTS

| | | |
|---|---|---|
| WO | WO 2011/120047 A1 | 9/2011 |
| WO | WO 2013/067221 A1 | 5/2013 |

OTHER PUBLICATIONS

Written Opinion issued in International Application No. PCT/2013/050346, entitled "Transpyloric Anchoring," Date of Written Opinion: Oct. 10, 2013.

International Preliminary Report on Patentability for International Application No. PCT/2013/050346, entitled "Transpyloric Anchoring," Issued Jan. 13, 2015.

\* cited by examiner

TRANSPYLORIC ANCHORING

RELATED APPLICATION

This application is the U.S. National Stage of International Application No. PCT/US2013/050346, filed Jul. 12, 2013, which designates the U.S., published in English, and claims the benefit of U.S. Provisional Application No. 61/671,470, filed on Jul. 13, 2012. The entire teachings of the above applications application are incorporated herein by reference.

BACKGROUND OF THE INVENTION

There is an ongoing need to improve the duration of time over which gastrointestinal implants may safely be anchored in the gastrointestinal tract without occlusion, migration or other malfunction or drawbacks, particularly for implants that extend over at least a portion of the intestines.

Examples of such implants include those having flexible (floppy) sleeves extending into the intestine such as presented in U.S. Pat. Nos. 7,025,791; 7,122,058; 7,476,256; 7,608,114; 7,706,973; 7,771,382; 7,815,589; 7,837,643; 8,057,420; and those having restrictive orifices as presented in U.S. Pat. No. 7,771,382. All of those patents are incorporated by reference in their entirety.

SUMMARY OF THE INVENTION

In accordance with an embodiment of the invention, there is provided a gastrointestinal implant device. The device comprises a planar proximal element configured to reside in a stomach to resist distal migration; a distal element configured to reside in an intestine to resist proximal migration; and one or more tethers coupling the planar proximal element to the distal element. A single tether is generally preferred.

The distal element may be configured to seal to tissue of the intestine, thereby channeling chyme from the stomach into the intestine. The planar proximal element may comprise a hoop. The distal element may comprise a wave anchor. The planar proximal element may be significantly larger than a diameter of a pylorus of the stomach in a first dimension, and may be smaller than the diameter of the pylorus in a second dimension, orthogonal to the first dimension. The planar proximal element may be between about 40 mm and about 100 mm in size in the first dimension; such as between about 50 mm and about 100 mm in size in the first dimension. The planar proximal element may be between about 1 mm and about 15 mm in size in the second dimension; for example, between about 1 mm and about 5 mm in size in the second dimension. The planar proximal element may comprise a hoop of between about 40 mm and about 60 mm diameter and of between about 0.5 mm and about 5 mm in thickness. The tether may comprise a flexible tether or a rigid tether. The planar proximal element may comprise a circular, polygon or an ellipsoid shape. The proximal element may be planar; for example, it may comprise at least one member of the group consisting of: a hoop, a polygon and an ellipsoid shape.

In further, related embodiments, the device may comprise no tissue penetrating features. The device may further comprise an unsupported, thin-walled sleeve coupled to the distal element. The sleeve may be floppy, flexible, conformable and collapsible. The planar proximal element may be without a seal to the stomach. In normal use of the implant device, a central longitudinal axis of the planar proximal element, perpendicular to a plane in which the planar proximal element lies, may be substantially perpendicular to a central longitudinal axis of a lumen of at least one of: a pyloric sphincter of the stomach; and the intestine. The distal element may comprise a three-dimensional object. The distal element may comprise a restrictor; and/or a fluid-filled chamber and/or a toroidal object. The distal element may comprise at least one of a catheter and a diagnostic device. The distal element may be between about 30 mm and about 40 mm in diameter. The distal element may comprise a wave anchor. The distal element may comprise a length to diameter ratio of at least about one. The distal element may comprise a length of between about 30 mm and about 40 mm; such as a length of at most about 32 mm, and may comprise an anchor of about the same length as the duodenal bulb. The distal element may comprise a spring element.| [A1].

In further related embodiments, at least one of the planar proximal element, the tether and the distal element may be covered in an atraumatic material, such as at least one of urethane and silicone. The tether may comprise a suture made of polymer or metal. The tether may be between about 10 mm and about 50 mm in length, and may be between about 0.5 mm and about 5 mm in diameter, such as between about 1 mm and about 2 mm in diameter. The distal element may comprise a plurality of spokes, and the tether may be coupled to the plurality of spokes. The distal element may be configured to change shape upon transmission of force to the distal element by the tether. The distal element may comprise a wave anchor, the tether being coupled to at least one crown of the wave anchor; such as the tether being coupled to a distal crown of the wave anchor, where the wave anchor comprises a diameter of between about 30 mm and about 40 mm. The distal element may be configured to open radially outwards upon exertion of tension by the tether to resist proximal migration. The planar proximal element may be loosely attached to the tether, thereby permitting the planar proximal element to rotate independently of the tether. The planar proximal element may be coupled to a tie loop to which the tether is coupled.

In further related embodiments, at least one of the planar proximal element and the distal element may comprise a polymer. The polymer may comprise at least one material of the group consisting of: silicone, polytetrafluoroethylene, polyethylene and polypropylene. At least one of the planar proximal element and the distal element may comprise a metal. The metal may comprise at least one of nitinol and stainless steel. The planar proximal element, distal element and tether may be configured to be collapsible into a container for endoscopic delivery into a gastrointestinal tract. At least one of the proximal element and the distal element may further comprise a removal drawstring.

There is provided a method of treatment comprising: with a planar proximal element in a stomach, resisting distal migration of a proximal portion of a gastrointestinal implant device into an intestine; with a distal element in the intestine, resisting proximal migration of a distal portion of the gastrointestinal implant device into the stomach; and with one or more tethers, securing the planar proximal element to the distal element across a pylorus. A single tether is generally preferred.

The method may further comprise sealing the distal element to tissue of the intestine, thereby channeling chyme from the stomach through the duodenal element into the intestine. The method may comprise securing the gastrointestinal implant device without penetrating tissue. The method may further comprise channeling chyme from the stomach into an unsupported, thin-walled sleeve extending into the intestine from the gastrointestinal implant device. The method may comprise resisting migration of the planar proximal element into the intestine without sealing the planar proximal element to the stomach. In the method, in normal use of the gastrointestinal implant device, a central longitudinal axis of the planar proximal element, perpendicular to a plane in which the planar proximal element lies, may be aligned to be substantially perpendicular to a central longitudinal axis of a lumen of at least one of: a pyloric sphincter of the stomach; and the intestine. The method may comprise restricting a flow of chyme from the stomach into the intestine using a restrictor coupled to the gastrointestinal implant device. The method may comprise retaining an anchor portion of the distal element within the duodenal bulb. The distal element may be configured to change shape upon transmission of force to the distal element by the tether; such as the distal element may be configured to open radially outwards upon exertion of tension by the tether. The planar proximal element may be loosely attached to the tether, thereby permitting the planar proximal element to rotate independently of the tether. The method may comprise delivering the planar proximal element, distal element and tether inside a container with an endoscope into a gastrointestinal tract.

There is provided a method of removing a gastrointestinal implant. The method comprises severing one or more tethers that couples a planar proximal element of the gastrointestinal implant in a stomach with a distal element of the gastrointestinal implant in an intestine; with a catheter, removing the planar proximal element proximally out of the stomach through a mouth; and with a grasper on a distal end of the catheter, grasping a drawstring to remove the distal element proximally out of the intestine, though the stomach and out of the mouth.

In further, related embodiments, removing the planar proximal element may comprise passing the planar proximal element through an overtube. Removing the distal element may comprise collapsing the distal element radially into a retrieval hood.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

There is provided an anchor for a gastrointestinal implant device. The anchor spans the pylorus, and therefore is called a transpyloric anchor. It is an objective of certain embodiments to provide the same or similar functionality as is provided by existing anchoring techniques for gastrointestinal implant devices, while having fewer side effects (such as bleeding, discomfort, migration and/or infection), and while having few or no tissue penetrating features.

Among other things, certain embodiments provide a method and apparatus for the application of a barrier sleeve in the digestive tract to limit the contact of food products in specific parts of the digestive tract and to provide enhanced satiety to patients with morbid obesity, enabling them to reduce their food intake. The sleeve may also be used for other treatments such as Type-2 diabetes through hormone triggers.

A rationale behind a transpyloric anchor in accordance with certain embodiments is that the antrum of the stomach is an advantageous location for a proximal element of the anchor; the duodenal bulb is an advantageous location for a distal element of the anchor; and the pylorus is a definite mechanical feature, which can be used for anchoring. The antrum of the stomach is adjacent to the pylorus and has tough tissue, while the duodenal bulb has minimal motion and permits the distal anchor to seal against tissue.

In a relaxed state, the stomach becomes flat, and thus a lightweight planar proximal element is able to orient itself in a plane within the relaxed stomach to cause as little trauma as possible to the stomach.

In accordance with certain embodiments, components of a transypyloric anchor include: (i) a planar proximal element in the stomach, which prevents distal migration; (ii) a distal element in the intestines, which both prevents proximal migration and may provide a seal; and (iii) one or more tethers, which connects the proximal and distal element.

Figure 1:
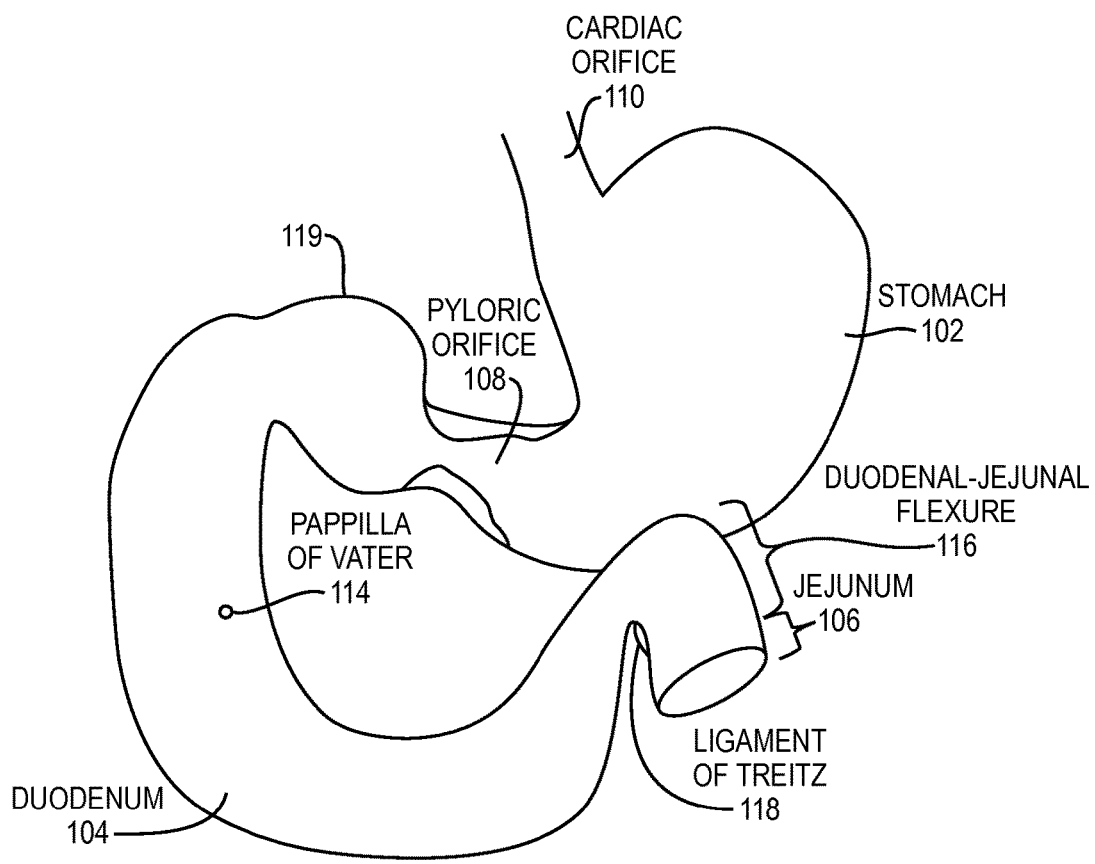
FIG. 1 is a sectional view of a portion of the digestive tract in a body.

FIG. 1 is a sectional view of a portion of the digestive tract in a body. Food to be digested enters the stomach 102 through the cardiac orifice 110 from the esophagus. Chyme, a semi-fluid, homogeneous creamy or gruel-like material produced by gastric digestion in the stomach exits the stomach through the pyloric orifice (pylorus) 108 and enters the small intestine 112. The pylorus 108 is a distal aperture of the stomach 102 surrounded by a strong band of circular muscle. The small intestine, about nine feet in length, is a convoluted tube, extending from the pylorus 108 to the ileo-caecal valve where it terminates in the large intestine. The small intestine has three sections, the duodenum 104, jejunum 106 and the ileum (not shown). The first eight to ten inch section of the small intestine 112, the duodenum 104, is the shortest, widest and most fixed part of the small intestine 112.

The duodenum 104 has four sections: superior, descending, transverse and ascending which typically form a U-shape. The superior section is about two inches long and ends at the neck of the gall bladder. The superior section also defines a feature referred to as the duodenal bulb 119 that begins just distal to the pylorus 108 and extends for about 1 to 1.5 inches in an adult human. The duodenal bulb 119 defines a lumen therein that is slightly larger than the distal duodenum 104. Advantageously, the duodenal bulb 119 exhibits less motion than the pylorus 108 and even distal portions of the duodenum 104. Notably, the motion is substantially limited to contractions without having a significant linear component (i.e., no movement along the central axis of the intestine). However, the tissue thins as one moves away from the pylorus 108.

The descending section of the duodenum 104 is about three to four inches long and includes a nipple shaped structure (papilla of Vater) 114 through which pancreatic juice from the pancreas and bile produced by the liver and stored by the gall bladder enter the duodenum from the pancreatic and bile ducts. The pancreatic juice contains enzymes essential to protein digestion and the bile dissolves the products of fat digestion. The ascending section is about two inches long and forms the duodenal-jejunal flexure 116 where it joins the jejunum 106, the next section of the small intestine. The duodenal-jejunal flexure 116 is fixed to the ligament of Treitz 118 (musculus supensionus duodeni). The juices secreted in the duodenum break the partially digested food down into particles small enough to be absorbed by the body. The digestive system is described in Gray's Anatomy ("Anatomy of the Human Body," by Henry Gray) and "Human Physiology," Vander, $3^{rd}$ ed, McGraw Hill, 1980, the contents of which are incorporated herein by reference in their entirety.

Figure 2:
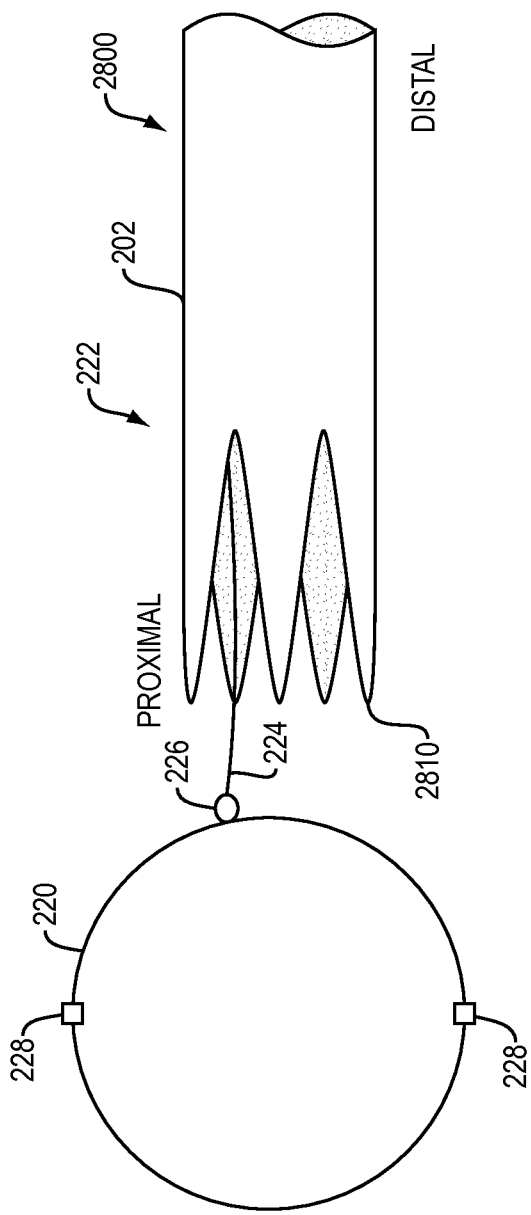
FIG. 2 is a perspective view of a gastrointestinal implant device with an embodiment of an anchoring device having a single tether and wave anchor distal element.

FIG. 2 is a perspective view of a gastrointestinal implant device 2800 comprising an anchoring device in accordance with an embodiment of the invention. The device 2800 comprises a planar proximal element 220 configured to reside in a stomach to resist distal migration; a distal element 222 configured to reside in an intestine to resist proximal migration and to provide a seal; and a single tether 224 coupling the planar proximal element 220 to the distal element 222.

In accordance with an embodiment of the invention, the planar proximal element 220 prevents distal migration only by being large enough that it cannot fit through the pylorus 108. In addition, a lack of leading edges inherent in this geometry makes it hard for the proximal element to push through the pylorus. There is no need for the proximal element 220 to form a seal to the stomach wall, nor for it to penetrate tissue of the stomach; and indeed, forces against the tissue required for sealing and members that penetrate tissue are undesirable in the proximal element 220 because the antrum of the stomach is a very active region that frequently undergoes contractions. The proximal element 220 can move relatively freely within the stomach (subject to the tether and contact with food and the walls of the stomach) without engaging tissue or forming a seal. By being planar, the proximal element 220 is atraumatic to the stomach tissue, since it orients in the plane of the stomach when the stomach is relaxed and without food and therefore typically the stomach is flat in this state. Likewise, the proximal element 220 should have as little mass as possible, in order to avoid trauma. The planar proximal element 220 may, for example, be a planar hoop or ring with an empty middle, as shown in FIG. 2. The hoop or ring may have a diameter between about 40 mm and about 100 mm. Using a diameter too small may risk the proximal element 220 migrating distally through the pylorus into the intestine; whereas using a diameter that is too large may risk producing trauma to the stomach. In one example, the proximal element may be a ring of about 60 mm diameter. The proximal element 220 should also be easy to deliver, which may be performed by bending the ring to fit within a container that can fit through the mouth and esophagus. The proximal element 220 is formed of a resilient material that can be deformed and return to its original shape. For example, the proximal element 220 may be formed of a metal such as stainless steel or Nitinol, or a polymer, such as polyethylene, polytetrafluoroethylene, polypropylene or silicone. The proximal element 220 may also be braided, such as a braided metal or polymer. In one example, the proximal element 220 is a ring of about 60 mm in diameter, formed of nitinol or stainless steel, coated with silicone or urethane. This could be a polymer coating or a tube that covers the element. A ring 220 may be formed by joining together nitinol components using one or more crimps 228 or by welding, and may then be covered with an atraumatic substance.

Figure 3:
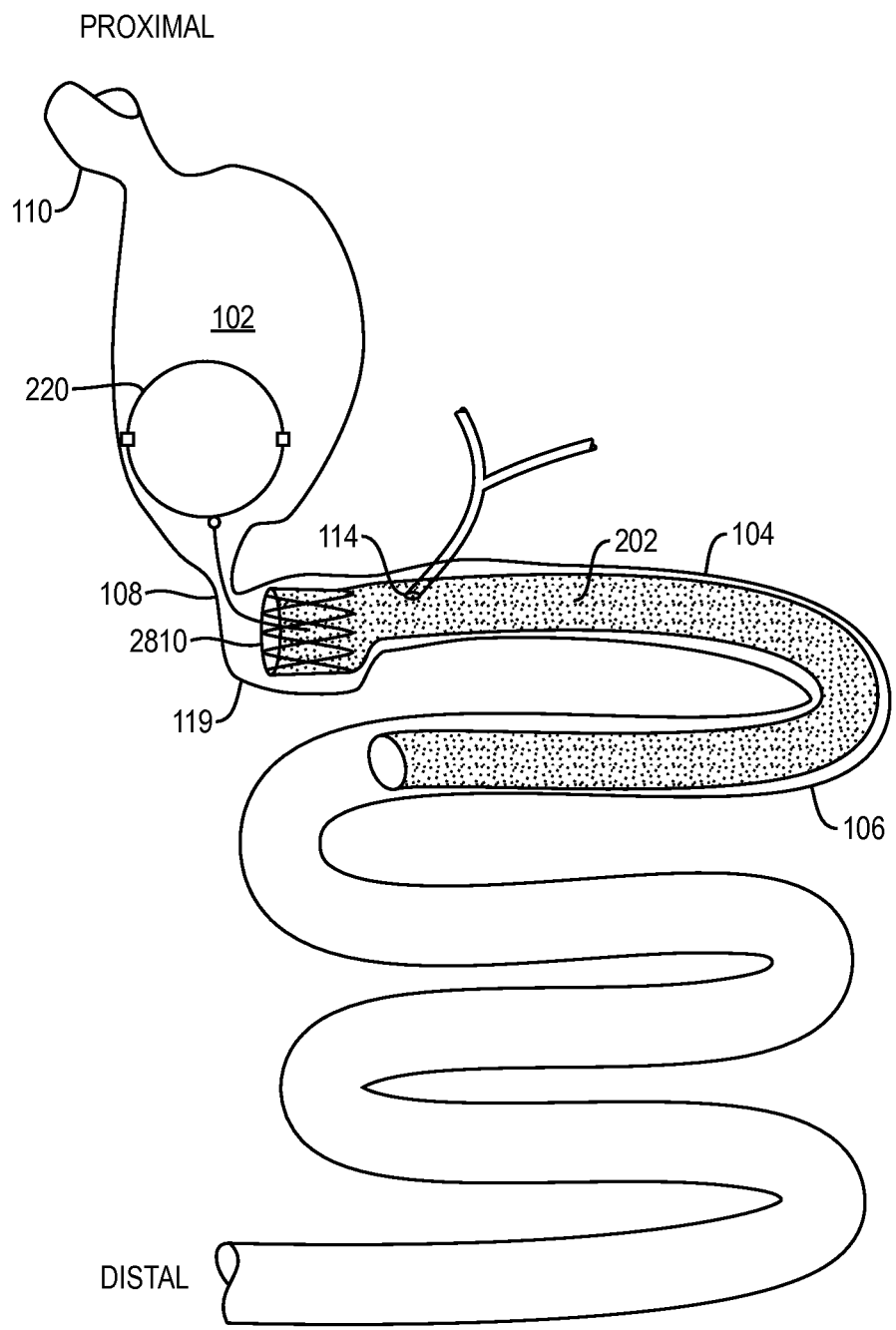
FIG. 3 is a sectional view of a body showing the gastrointestinal implant device of FIG. 2 implanted in the digestive system.

In accordance with an embodiment of the invention, the proximal element 220 may be normally oriented perpendicular to the lumen of the pyloric sphincter or the intestinal lumen, as shown in FIG. 3. More specifically, in normal use of the implant device, a central longitudinal axis of the planar proximal element, perpendicular to a plane in which the planar proximal element lies, is substantially perpendicular to a central longitudinal axis of a lumen of pyloric sphincter of the stomach, or of the intestine. Because the proximal element 220 moves relatively freely, subject to tension from the tether and contact with chyme and the stomach walls, it will also be oriented at a variety of different angles in use.

While the planar proximal element 220 is described as "planar" it has some thickness in practice. The planar proximal element is significantly larger than a diameter of a pylorus of the stomach in a first dimension, and is smaller than the diameter of the pylorus in a second dimension, orthogonal to the first dimension. For example, the planar proximal element may be between about 40 mm and about 100 mm in size in the first dimension (e.g., diameter); such as between about 50 mm and about 100 mm in size in the first dimension (e.g., diameter); and between about 0.5 mm and about 15 mm in size in the second dimension (e.g., thickness and bending), such as between about 1 mm and about 5 mm in size in the second dimension (e.g., thickness). In one example, the planar proximal element comprises a hoop of between about 40 mm and about 60 mm diameter and of between about 1 mm and about 5 mm in thickness. The planar proximal element may comprise other planar shapes in addition to a ring or hoop, such as a polygon or an ellipsoid shape.

In accordance with an embodiment of the invention, the distal element 222 has the purpose of both sealing to the tissue of the intestines, and preventing proximal migration. By forming a seal, the distal element 222 permits chyme to be channeled into the distal element without contacting the walls of the intestines, thereby forming an intestinal bypass. The distal element 222 may be a three dimensional object, such as a wave anchor 2810 (shown in FIG. 2), to which an unsupported, flexible sleeve 202 may be attached. The sleeve may be floppy, flexible, conformable and collapsible. For example, the sleeve may be one taught in U.S. Pat. No. 7,981,163 B1, the entire disclosure of which is hereby incorporated herein by reference, or any of the previously cited U.S. patents. The distal element 222 may also be another three dimensional object, such as a balloon and/or a toroidal element, and may include a fluid-filled chamber. For example, the distal element may be a fluid-filled toroidal element such as those taught in U.S. Patent App. No. 2011/0004228 A1 of Priplata et al., the entire disclosure of which is hereby incorporated herein by reference. The distal element 222 may support a restrictive element, such as a plate resistor, which may be combined with a sleeve. The resistor extends across the anchor or a sleeve and has one or more restrictive apertures therein. Further, the distal element 222 may support a catheter or a diagnostic device, such as a pressure sensor. The diameter of the distal element 222, such as a wave anchor, may be between about 30 mm and 40 mm, in order to avoid trauma to the intestine. For example, the diameter may be about 35 mm. The length to diameter ratio of the distal element 222 may be about one. In length, the distal element 222 may be of about the same length as the duodenal bulb 119, in order to fit within that anatomical feature. The wave anchor may comprise a single wave of a few cycles, five being shown. The wave may be formed of collapsible wire, such as of metal such as Nitinol. The distal element 222 may include no tissue penetrating features, such as barbs, and may be coated or covered with an atraumatic substance such as silicone or urethane.

In another embodiment according to the invention, the distal element 222 may be planar. For example, the distal element may be a hoop, a polygon or an ellipsoid shape. This shape would not provide a seal, but would provide atraumatic anchoring.

In accordance with an embodiment of the invention, the purpose of the tether 224 is to couple the proximal element 220 to the distal element 222. Using a single tether 224 provides the advantage of avoiding tangling, as could occur if multiple tethers were to be used. The tether 224 may be flexible such as a suture or may be rigid, such as a rod. Regardless of whether flexible or rigid, the tether 224 may be attached at its proximal end to a tie loop 226, which permits the proximal element 220 to rotate independently of the tether 224 by sliding through loop 226. The tether 224 is between about 10 mm and about 50 mm in length. If the tether is too short, it may force the pylorus open, causing discomfort, but if it is too long, it may permit the distal element 222 to move too far into the intestine, such as out of the duodenal bulb. The tether has a diameter of between about 0.5 mm and about 5 mm, such as between about 1 mm and about 2 mm. A diameter that is too large may cause the pylorus to sense the tether. If too small, it could cause cutting of the tissues. In one example, the tether is a suture. The tether may be attached at its distal end to the center of a set of spokes, such as spokes made of sutures, which extend to the inner periphery of the distal element 222. The tether may, for example, be formed of polypropylene braid, or polyethylene or ptfe; and may be either uncovered or covered, for example with silicone, ePTFE or urethane to prevent trauma.

In another embodiment, the tether 224 may be attached at its distal end to the distal element 222 in a way that causes the distal element 222 to change its shape. For example, where the distal element 222 is a wave anchor, the tether 224 may be coupled to a distal crown of the wave anchor, which tends to cause the wave anchor to open radially outwards at its proximal end when the tether 224 exerts tension on the distal element 222. In this way, the distal element 222 actively resists proximal migration. Other active elements may be used for the distal element 222.

In the embodiment of FIG. 2, the gastrointestinal implant device 2800 includes a sleeve 202 and an anchoring device 2810 for anchoring the gastrointestinal implant 2800 device in the duodenum 104. The anchoring device 2800 includes a wave anchor 2810 coupled to a proximal portion of the sleeve 202. The wave anchor 2810 includes a compliant, radial spring shaped into an annular wave pattern about a central axis, providing an outward radial force, while allowing substantial flexure about its perimeter. Such flexure is advantageous as it may be collapsed radially to allow for minimally-invasive delivery and ensures that the device will substantially conform to the surrounding anatomical structure when implanted and allowed to expand. The annular wave element can be formed from one or more elongated resilient members and defines a lumen along its central axis formed between two open ends.

When implanted, as shown in FIG. 3, the proximal element 220 moves substantially freely in the stomach, while the central axis of the distal element's anchor 2810 is substantially aligned with the central axis of the duodenum 104, allowing chyme to pass through the device 2800. Additionally, the compliant wave anchor 2810 minimizes trauma to the tissue by providing sufficient flexibility and compliance, while minimizing the likelihood of tissue erosion.

The compliant wave anchor 2810 can be manufactured from a resilient metal such as a heat-treated spring steel, stainless steel, or from an alloy such as NiTi alloy commonly referred to as Nitinol. Other alloys include nickel-cobalt-chromium-molybdenum alloys possessing a unique combination of ultrahigh tensile strength, such as MP35N. Additionally, the wave anchor 2810 can be formed from a polymer and/or a composite having similar properties. The wave anchor 2810 can be manufactured from a single strand, such as a wire, contoured into the desired shape. Alternatively, the wave anchor 2810 can be manufactured from multi-strands of the same or different materials similarly contoured to the desired shape. In some embodiments, the wave anchor 2810 can be cut into the wave shape from tubular stock of the desired material, such as Nitinol.

When implanted, the anchor 2810 can enable a sleeve 202, or barrier to be securely implanted within the duodenum 104, preferably providing a fluid seal at the proximal end. To enhance a fluid seal, the proximal end of the sleeve can be contoured to the wave anchor as shown in FIG. 2. For a device 2800 using a sleeve 202 contoured to the wave anchor 2810, the proximal end appears tulip-shaped.

In an embodiment according to the invention, the proximal element 220 may prevent the device from migrating distally, but may be without a seal, whereas the distal element 222 is used to form a seal against tissue, such as the duodenal wall.

In one example, the distal element 222 is a 32-33 mm diameter wave anchor, with five peaks, formed from wire of 0.032-0.035 inches. The hoop 220 may, for example, be 0.034 inches thick, formed of two loops with two crimps; or 0.025 inches thick, formed of three loops with two crimps.

In another example, the proximal element 220 comprises 2 loops of 0.040" diameter wire, crimped together in two spots, 180 degrees opposed, with a 60 mm diameter overall loop; while the distal element 222 comprises a 35 mm diameter wave anchor, with a greater than one pound compliance and formed of 0.030" diameter wire. A wave anchor as large as 55 mm diameter may also be used, with no tissue engaging barbs. It will be appreciated that a variety of different diameters, wire thicknesses, compliances and number of crowns for a wave anchor may be used (for example, five or six crowns on the wave anchor).

Figure 4:
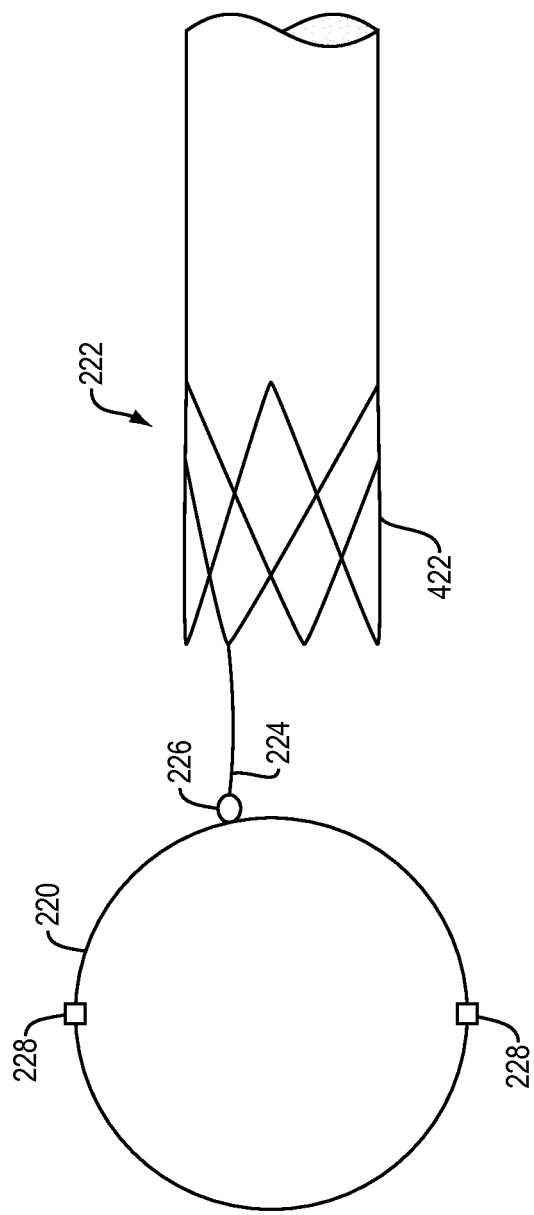
FIG. 4 is gastrointestinal implant devices in accordance with another embodiment of the invention having a single tether and stent distal element.

In FIG. 4, the distal element 222 comprises a stent 442.

Figure 5:
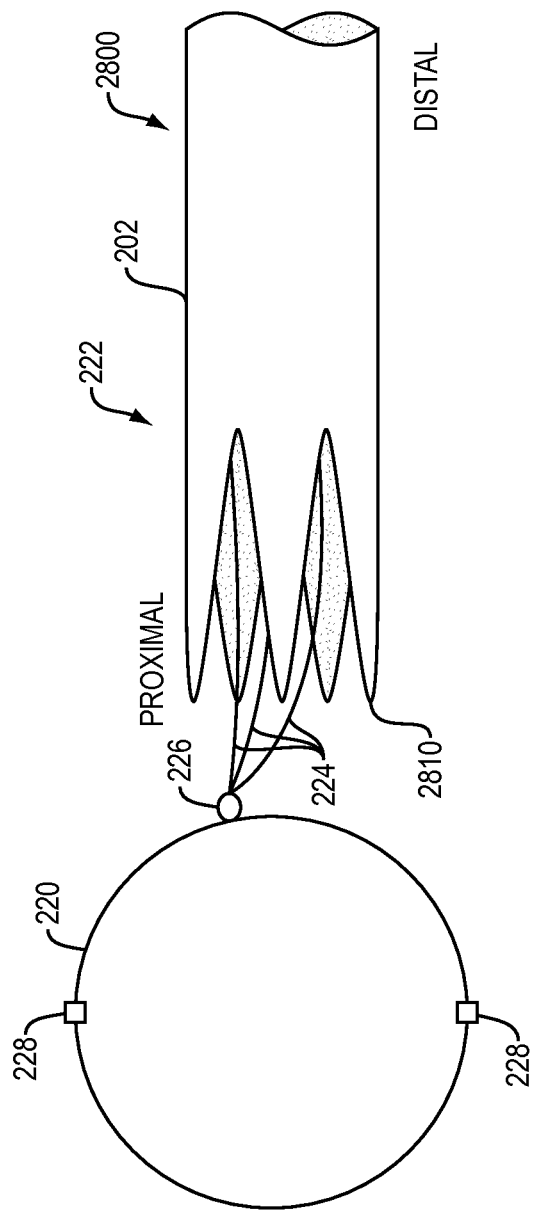
FIG. 5 is an implant device of the invention having plural tethers.

FIG. 5 shows an embodiment in which the wave anchor 2810 is tethered with two tethers. This is less preferred for reasons expressed above but may have some application.

Figure 6:
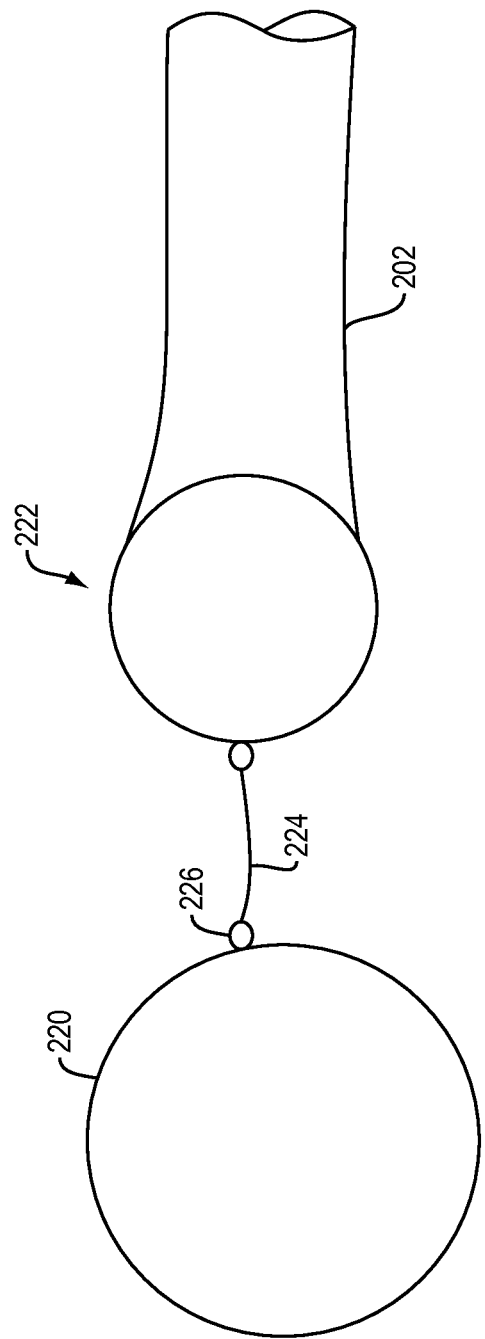
FIG. 6 is an implant device of the invention having a planar distal element.

FIG. 6 shows an embodiment in which the distal element 222 is also planar. The planar distal element serves to retain the device against proximal movement but does not provide fluid sealing against the intestine.

Figure 7:
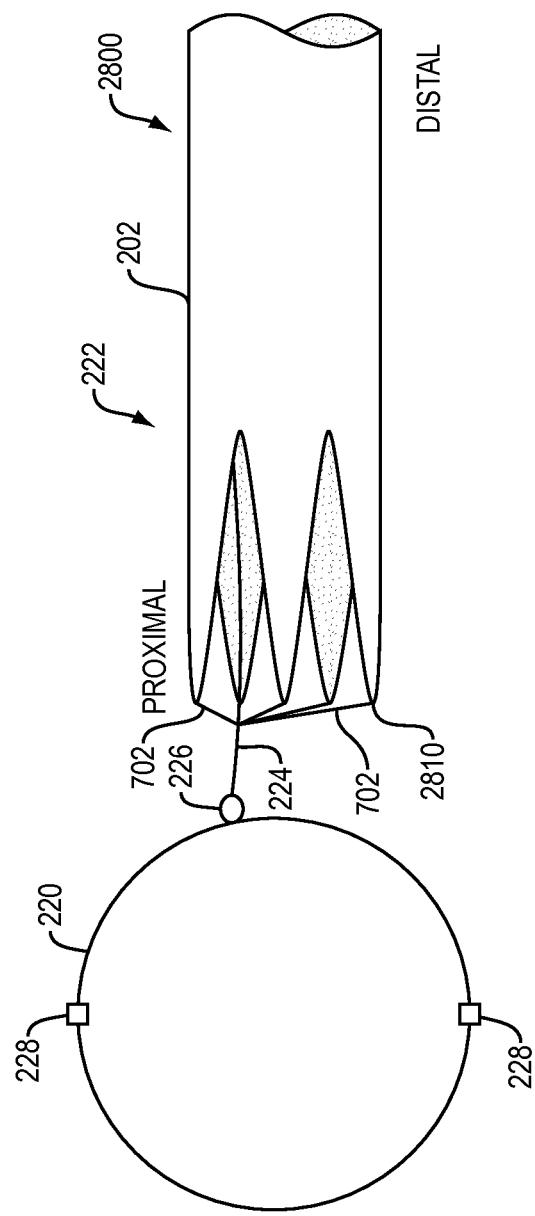
FIG. 7 is an implant device of the invention in which the tether is coupled to spokes on the distal element.

FIG. 7 shows an embodiment in which the tether is coupled to spokes 702 on the distal element.

The planar proximal element, distal element and tether are configured to be collapsible into a container for delivery through the mouth and esophagus into a gastrointestinal tract. For example, container delivery techniques may be used such as those taught in U.S. Pat. No. 7,837,643 B2 of Levine et al., the entire disclosure of which is hereby incorporated herein by reference.

In an embodiment according to the invention, the device may be removed by cutting the tether 224, and then pulling the proximal element 220 (such as a hoop) through the esophagus, for example through an esophageal overtube. The proximal element 220 (such as a hoop) can be cut or undone to assist in removal. Alternatively, suture material may be used in one or more components, which may be cut to assist in removal. The device may be able to be removed without an overtube. Further, the foregoing methods may be used to remove the proximal element 220, while another method of removal is used for the distal element 222, for instance using a drawstring 2810 (FIG. 3) technique as set forth in U.S. Pat. No. 8,057,420, the entire disclosure of which is hereby incorporated herein by reference. The proximal element and/or the distal element further may comprise a removal drawstring.

In one embodiment, a method of removing a gastrointestinal implant comprises severing one or more tethers that couples a planar proximal element of the gastrointestinal implant in a stomach with a distal element of the gastrointestinal implant in an intestine; with a catheter, removing the planar proximal element proximally out of the stomach through a mouth; and with a grasper on a distal end of the catheter, grasping a drawstring to remove the distal element proximally out of the intestine, though the stomach and out of the mouth. The planar proximal element may be removed through an overtube. The distal element may be collapsed radially into a retrieval hood. The proximal element may also be collapsed in a retrieval hood for removal.

In accordance with an embodiment of the invention, there is provided a method of treatment. The method comprises providing a gastrointestinal implant device set forth herein, and securing the device across the pylorus of a patient. Chyme may be channeled from the stomach into an unsupported, thin-walled sleeve extending into the intestine from the gastrointestinal implant device. For example, a sleeve such as those set forth in U.S. Pat. No. 7,682,330 (the entire disclosure of which is hereby incorporated herein by reference) may be used. Further, a flow of chyme from the stomach into the intestine may be restricted with a restrictor coupled to the gastrointestinal implant device. For example, a restrictor such as those set forth in U.S. Pat. No. 7,771,382 (the entire disclosure of which is hereby incorporated herein by reference) may be used.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A gastrointestinal implant device comprising:
   a planar proximal element configured to reside in a stomach to resist distal migration;
   a distal element configured to reside in an intestine to resist proximal migration; and
   one or more tethers coupling the planar proximal element to the distal element;
   wherein the planar proximal element is between 40 mm and 100 mm in size in a first dimension, and is between 0.5 mm and 15 mm in size in a second dimension, orthogonal to the first dimension;
   and wherein, in normal use of the implant device, a central longitudinal axis of the planar proximal element, perpendicular to a plane in which the planar proximal element lies, is substantially perpendicular to a central longitudinal axis of a lumen of a pyloric sphincter of the stomach.

2. The gastrointestinal device of claim 1, wherein only a single tether couples the planar proximal element to the distal element.

3. The gastrointestinal implant device of claim 1, wherein the distal element is configured to seal to tissue of the intestine, thereby channeling chyme from the stomach into the intestine.

4. The gastrointestinal implant device of claim 1, wherein the planar proximal element comprises a hoop.

5. The gastrointestinal implant device of claim 1, wherein the distal element comprises a wave anchor.

6. The gastrointestinal implant device of claim 1, wherein the planar proximal element is between 50 mm and 100 mm in size in the first dimension.

7. The gastrointestinal implant device of claim 1, wherein the planar proximal element is between 0.5 mm and 5 mm in size in the second dimension.

8. The gastrointestinal implant device of claim 1, wherein the planar proximal element comprises a hoop of between about 40 mm and about 60 mm diameter and of between about 0.5 mm and about 5 mm in thickness.

9. The gastrointestinal implant device of claim 1, wherein the tether comprises a flexible tether.

10. The gastrointestinal implant device of claim 1, wherein the tether comprises a rigid tether.

11. The gastrointestinal implant device of claim 1, wherein the planar proximal element comprises a polygon or an ellipsoid shape.

12. The gastrointestinal implant device of claim 1, wherein the distal element is planar.

13. The gastrointestinal implant device of claim 12, wherein the distal element comprises at least one member of the group consisting of: a hoop, a polygon and an ellipsoid shape.

14. The gastrointestinal implant device of claim 1, wherein the device comprises no tissue penetrating features.

15. The gastrointestinal implant device of claim 1, further comprising an unsupported, thin-walled sleeve coupled to the distal element.

16. The gastrointestinal implant device of claim 1, wherein the planar proximal element is without a seal to the stomach.

17. The gastrointestinal implant device of claim 1, wherein the distal element comprises a restrictor.

18. The gastrointestinal implant device of claim 1, wherein the distal element comprises a fluid-filled chamber.

19. The gastrointestinal implant device of claim 1, wherein the distal element comprises a toroidal object.

20. The gastrointestinal implant of claim 1, wherein the distal element comprises at least one of a catheter and a diagnostic device.

21. The gastrointestinal implant device of claim 1, wherein the distal element is between 30 mm and 40 mm in diameter.

22. The gastrointestinal implant device of claim 1, wherein the distal element comprises a length to diameter ratio of at least about one.

23. The gastrointestinal implant device of claim 1, wherein the distal element comprises a length of between 30 mm and 40 mm.

24. The gastrointestinal implant device of claim 1, wherein the distal element comprises a length of at most 32 mm.

25. The gastrointestinal implant device of claim 1, wherein the distal element comprises an anchor of about the same length as the duodenal bulb.

26. The gastrointestinal implant device of claim 1, wherein at least one of the planar proximal element, the tether and the distal element is covered in an atraumatic material.

27. The gastrointestinal implant device of claim 1, wherein the tether comprises a suture.

28. The gastrointestinal implant device of claim 1, wherein the tether is between 10 mm and 50 mm in length.

29. The gastrointestinal implant device of claim 1, wherein the tether is between 0.5 mm and 5 mm in diameter.

30. The gastrointestinal implant device of claim 29, wherein the tether is between 1 mm and 2 mm in diameter.

31. The gastrointestinal implant device of claim 1, wherein the distal element comprises a plurality of spokes, and wherein the tether is coupled to the plurality of spokes.

32. The gastrointestinal implant device of claim 1, wherein the distal element is configured to change shape upon transmission of force to the distal element by the tether.

33. The gastrointestinal implant device of claim 1, wherein the distal element comprises a wave anchor, the tether being coupled to at least one crown of the wave anchor.

34. The gastrointestinal implant device of claim 33, wherein the tether is coupled to a distal crown of the wave anchor, and wherein the wave anchor comprises a diameter of between about 30 mm and about 40 mm.

35. The gastrointestinal implant device of claim 1, wherein the distal element is configured to open radially outwards upon exertion of tension by the tether.

36. The gastrointestinal implant device of claim 1, wherein the planar proximal element is loosely attached to the tether, thereby permitting the planar proximal element to rotate independently of the tether.

37. The gastrointestinal implant device of claim 1, wherein the planar proximal element is coupled to a tie loop to which the tether is coupled.

38. The gastrointestinal implant device of claim 1, wherein the planar proximal element, distal element and tether are configured to be collapsible into a container for endoscopic delivery into a gastrointestinal tract.

39. The gastrointestinal implant device of claim 1, wherein at least one of the proximal element and the distal element further comprises a removal drawstring.

40. A method of treatment comprising:
  with a planar proximal element in a stomach, resisting distal migration of a proximal portion of a gastrointestinal implant device into an intestine;
  with a distal element in the intestine, resisting proximal migration of a distal portion of the gastrointestinal implant device into the stomach; and
  with one or more tethers, securing the planar proximal element to the distal element across a pylorus;
  wherein the planar proximal element is between 40 mm and 100 mm in size in a first dimension, and is between 0.5 mm and 15 mm in size in a second dimension, orthogonal to the first dimension;
  and wherein, in normal use of the implant device, a central longitudinal axis of the planar proximal element, perpendicular to a plane in which the planar proximal element lies, is substantially perpendicular to a central longitudinal axis of a lumen of a pyloric sphincter of the stomach.

41. The method of treatment of claim 40 wherein only a single tether secures the planar proximal element to the distal element.

42. The method of treatment of claim 40, further comprising sealing the distal element to tissue of the intestine, thereby channeling chyme from the stomach into the intestine.

43. The method of treatment of claim 40, comprising securing the gastrointestinal implant device without penetrating tissue.

44. The method of treatment of claim 40, further comprising channeling chyme from the stomach into an unsupported, thin-walled sleeve extending into the intestine from the gastrointestinal implant device.

45. The method of treatment of claim 40, comprising resisting migration of the planar proximal element into the intestine without sealing the planar proximal element to the stomach.

* * * * *